United States Patent [19]

Horwell et al.

[11] Patent Number: 4,705,807

[45] Date of Patent: Nov. 10, 1987

[54] AMINE DERIVATIVES

[75] Inventors: David C. Horwell, Farnborough; Graham H. Timms, Mytchett, both of England

[73] Assignee: Lilly Industries Limited, London, England

[21] Appl. No.: 448,549

[22] Filed: Dec. 10, 1982

Related U.S. Application Data

[63] Continuation of Ser. No. 277,541, Jun. 26, 1981, abandoned, which is a continuation of Ser. No. 93,701, Nov. 13, 1979, abandoned, which is a continuation of Ser. No. 943,083, Sep. 18, 1978, abandoned, which is a continuation-in-part of Ser. No. 683,873, May 6, 1976, abandoned.

[30] Foreign Application Priority Data

May 8, 1975 [GB] United Kingdom ............... 19348/75

[51] Int. Cl.[4] ..................... A61K 31/455; C07C 87/28
[52] U.S. Cl. .................................. 514/650; 260/501.1; 564/338
[58] Field of Search ................ 564/338; 424/315, 330; 260/501.1; 514/650

[56] References Cited

U.S. PATENT DOCUMENTS

| | | | |
|---|---|---|---|
| 3,133,901 | 5/1964 | Poos | 564/305 X |
| 3,308,160 | 3/1967 | Snyder | 564/308 |
| 3,362,878 | 1/1967 | Snyder | 564/308 X |
| 3,413,348 | 11/1968 | Gregory et al. | 564/308 |
| 3,742,055 | 6/1973 | Freedman | 564/308 |
| 3,980,785 | 9/1976 | Wildsmith | 564/308 |

FOREIGN PATENT DOCUMENTS

| | | | |
|---|---|---|---|
| 873018 | 7/1961 | United Kingdom | 564/308 |
| 992734 | 5/1965 | United Kingdom | 564/308 |

OTHER PUBLICATIONS

Roll et al., "Proton Magnetic Resonance Spectra and Stereochemistry of Some 5,6-Disubstituted Bicyclo [2.2.2]oct-2-enes," *J. Pharm. Sci.* 54 (8), 1110–1117 (1965).

P. N. Patil et al., "Molecular Geometry and Adrenergic Drug Activity," *Pharmacological Reviews* 26 (4), 323–334, 348–355 (1975).

Burger, "Medicinal Chemistry," vol. II, 3rd Ed., pp. 1471–1472, 1478–1480, 1490–1492, (1970).

Roos et al., "5-Hydroxyindolacetic Acid (and Homovanillic Acid Levels in the Cerebrospinal Fluid after Probenecid Application in Patients with Manic–Depressive Psychosis," *Chem. Abstr.* 71:79688c (1969).

Pullar, "Amine Metabolism in Affective Disorders," *Biochem. Soc. Spec. Publ.* 1, 97–100 (1973).

Papeschi et al., "Homovanillic and 5-Hydroxyindoleacetic Acid in Cerebrospinal Fluid of Depressed Adults," *Arch. Gen. Psychiat.* 25, 354–357 (1971).

Bunney et al., "Effect of L-Dopa on Depression," *Lancet* 1, 885–886 (1969).

Bunney et al., "L-Dopa in Depressed Patients," *Lancet* 1, 352 (1970).

Clark et al., "Drugs and Psychiatry: a New Era," *Newsweek*, Nov. 12, 1979, pp. 98–104.

*Primary Examiner*—Robert V. Hines
*Attorney, Agent, or Firm*—Nancy J. Harrison; Leroy Whitaker

[57] ABSTRACT

Novel amines of formula:

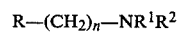

$$R-(CH_2)_n-NR^1R^2$$

where R is cis-2-phenylbicyclo[2,2,2]octane or 2-phenylbicyclo[2,2,2]oct-2-ene nucleus, n is 1 to 3, $R^1$ is $C_{1-3}$ alkyl and $R^2$ is hydrogen or $C_{1-3}$ alkyl, and acid-addition salts thereof, which are useful for the treatment of disorders of the central nervous system.

9 Claims, No Drawings

AMINE DERIVATIVES

CROSS REFERENCE TO RELATED APPLICATION

This application is a continuation of application Ser. No. 277,541, filed June 26, 1981, which is a continuation of application Ser. No. 93,701 filed Nov. 13, 1979, which is a continuation of application Ser. No. 943,083, filed Sept. 18, 1978, which is a continuation-in-part of application Ser. No. 683,873, filed May 6, 1976 all now abandoned.

DETAILED DESCRIPTION

This invention relates to a novel class of 2-phenyl-bicyclooctane and ocetne derivatives having useful central nervous system activity. The invention also provides methods by which such novel compounds may be prepared, novel intermediates useful in the preparation of the active compounds, as well as methods of treating disorders of the central nervous system therewith.

In U.S. Pat. No. 3,980,785 there is described and claimed a class of trans-derivatives which also possess a 2-phenylbicyclooctane nucleus and which have activity in the central nervous system. U.S. Pat. Nos. 3,308,160 and 3,362,878 also disclose bicyclooctanes having central nervous system activity.

According to the present invention there is provided an amine of formula (I):

R—(CH$_2$)$_n$—NR$^1$R$^2$  (I)

or an acid-addition salt thereof, wherein n is an integer from 1 to 3, R$^1$ is C$_{1-3}$ alkyl, R$^2$ is hydrogen or C$_{1-3}$ alkyl and R is a 2-phenylbicyclo group of formula:

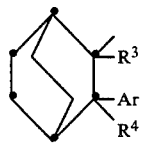

(II)

wherein R$^3$ and R$^4$ each represent a hydrogen atom, said hydrogen atoms being in a cis-relationship, or taken together represent a single chemical bond; and wherein Ar is seelcted from the group consisting of phenyl, p-halophenyl, and 3,4-dihalophenyl.

When R$^3$ and R$^4$ represent cis-hydrogen atoms the Ar and —(CH$_2$)$_n$NR$^1$R$^2$ groups will also be in a cis-relationship. Such cis-2-phenylbicyclooctanes of formula (I) may be represented by the formula (III):

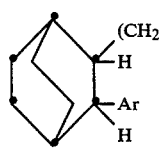

(III)

Those skilled in the art will appreciate that the compounds of formula (III) may exist in two enantiomeric forms and it is to be clearly understood that the invention extends to both the (+) or (−) form, as well as the racemic mixture thereof.

When R$^3$ and R$^4$ taken together represent a single chemical bond the 2-phenylbicyclooct-2-ene of formula (I) may be represented by the formula (IV):

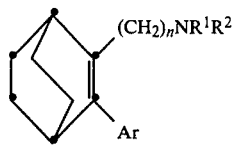

(IV)

Preferred compounds of formula (I) are those having one or more of the following features:
(a) n is 1;
(b) R$^1$ is C$_{1-3}$ alkyl and R$^2$ is hydrogen, methyl or ethyl;
(c) R$^1$ and R$^2$ are the same or different C$_{1-3}$ alkyl groups;
(d) R$^1$ and R$^2$ are methyl;
(e) R$^3$ and R$^4$ are cis-hydrogen atoms;
(f) Ar is phenyl substituted by halogen in the 3,4-position;
(g) Ar is a p-chloro or p-bromophenyl group;
(h) Ar is 3,4-dichlorophenyl; or
(i) R$^3$ and R$^4$ are cis-hydrogen atoms and the compound of formula (I) is the (+)-enantiomer.

Most advantageously, the compounds of formula (I) have the features (a), (b), (e) and (g); (a), (b) and (f); (a), (d), (g) and (i); (a), (d) and (g); or (a), (d), (h) and (i).

For the avoidance of doubt, the term "C$_{1-3}$ alkyl" as used herein is intended to encompass any straight or branched chain alkyl group having from 1 to 3 carbon atoms. Thus R$^1$ and/or R$^2$ may be a methyl, ethyl, n-propyl, or isopropyl group. Similarly, the terms "halogen" or "halo" refere to fluorine, chlorine, or bromine.

Presently preferred compounds of the invention are:
cis-3-N,N-dimethylaminomethyl-2-(p-chlorophenyl)-bicyclo[2,2,2]octane;
cis-3-N-methylaminomethyl-2-(p-chlorophenyl)-bicyclo[2,2,2]octane;
cis-3-N,N-dimethylaminomethyl-2-(3,4-dichlorophenyl)-bicyclo[2,2,2]octane;
cis-3-N-methylaminomethyl-2-(3,4-dichlorophenyl)-bicyclo[2,2,2]octane;
cis-3-N,N-dimethylaminomethyl-2-(p-bromophenyl)-bicyclo[2,2,2]octane;
cis-3-N-methylaminomethyl-2-(p-bromophenyl)-bicyclo[2,2,2]octane; and their (+)-enantiomers;
3-N-methylaminomethyl-2-(3,4-dichlorophenyl)-bicyclo[2,2,2]oct-2-ene; and
3-N,N-dimethylaminomethyl-2-(3,4-dichlorophenyl)-bicyclo[2,2,2]oct-2-ene.

Other illustrative examples of compounds of the invention are;
cis-3-N,N-diethylaminomethyl-2-(3,4-dichlorophenyl)-bicyclo[2,2,2]octane;
cis-3-N-ethylaminomethyl-2-(3,4-dichlorophenyl)-bicyclo[2,2,2]octane;
cis-3-N-methylaminoethyl-2-phenylbicyclo[2,2,2]octane;
cis-3-N,N-dimenthylaminoethyl-2-phenylcyclo[2,2,2]octane;
cis-3-N-methylaminoethyl-2-(p-chlorophenyl)-bicyclo[2,2,2]octane;
cis-3-N,N-dimethylaminoethyl-2-(p-chlorophenyl)-bicyclo[2,2,2]octane;

cis-3-N-methylaminoethyl-2-(3,4-dichlorophenyl)-bicyclo[2,2,2]octane;
cis-3-N,N-dimethylaminoethyl-2-(3,4-dichlorophenyl)-bicyclo[2,2,2]octane;
cis-3-N,N-dimethylaminoethyl-2-(3,4-difluorophenyl)-bicyclo[2,2,2]octane;
cis-3-N-methylaminopropyl-2-phenylbicyclo[2,2,2]octane;
cis-3-N,N-dimethylaminopropyl-2-phenylbicyclo[2,2,2]octane;
3-N-methylaminomethyl-2-phenylbicyclo[2,2,2]oct-2-ene;
3-N,N-dimethylaminomethyl-2-phenylbicyclo[2,2,2]oct-2-ene;
3-N,N-diethylaminomethyl-2-(3,4-dichlorophenyl)-bicyclo[2,2,2]oct-2-ene;
3-N-ethylaminomethyl-2-(3,4-dichlorophenyl)-bicyclo[2,2,2]oct-2-ene;
3-N-methylaminoethyl-2-phenylbicyclo[2,2,2]oct-2-ene;
3-N,N-dimethylaminoethyl-2-phenylbicyclo[2,2,2]oct-2-ene;
3-N-methylaminoethyl-2-(p-chlorophenyl)bicyclo[2,2,2]oct-2-ene;
3-N,N-dimethylaminoethyl-2-(p-chlorophenyl)bicyclo[2,2,2]oct-2-ene;
3-N-methylaminoethyl-2-(3,4-dichlorophenyl)-bicyclo[2,2,2]oct-2-ene;
3-N,N-dimethylaminoethyl-2-(3,4-dichlorophenyl)-bicyclo[2,2,2]oct-2-ene;
3-N,N-dimethylaminoethyl-2-(3,4-difluorophenyl)-bicyclo[2,2,2]oct-2-ene;
3-N-methylaminopropyl-2-phenylbicyclo[2,2,2]oct-2-ene;
3-N,N-dimethylaminopropyl-2-phenylbicyclo[2,2,2]oct-2-ene;
and their acid-addition salts, especially their pharmaceutically-acceptable salts.

The compounds of formula (I) may be prepared by any of the normal methods for preparing substituted alkyl amines.

According to one aspect of the present invention there is provided a method of preparing a compound of formula (I), or an acid-addtion salt thereof, where comprises
(A) reducing:
(i) a compound of formula (V):

R—(CH$_2$)$_m$—Z   (V)

where m is 0, 1 or 2 and Z is —CONR$^1$R$^2$, —CH=NR$^1$ or —C(OR$^1$)=NR$^1$; or
(ii) an olefin of formula (VI):

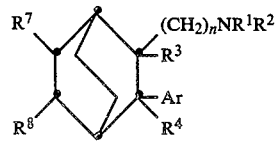   (VI)

where R$^7$ and R$^8$ taken together represent a single bond or, when R$^3$ and R$^4$ taken together represent a single bond, independently represent hydrogen atoms;
(B) alkylating a compound of formula (VII):

R—(CH$_2$)$_n$NHR$^2$   (VII)

or (C) condensing an amine of formula:

HNR$^1$R$^2$ with a compound of formula (VIII):

R—(CH$_2$)$_n$—Q   (VIII)

where Q is a leaving group;

optionally followed when R$^3$ and R$_4$ represent cis-hydrogen atoms by (D) resolution of the product of formula (I) formed in reaction (A), (B) or (C), into its (+) or (−) enantiomeric form.

The preferred methods of preparation according to the present invention involve the use of an intermediate of formula (IX):

R—(CH$_2$)$_m$—Z'   (IX)

where m is as defined above, i.e. n−1, and Z' represents Z or —CHO, —CN, —COCl, —CONH$_2$, —CH$_2$NCO or —COOR$^9$ where R$^9$ is C$_{1-4}$ alkyl, which may, if convenient, be reacted in situ in the reaction medium in which it is formed.

When R is a biocyclooctane nucleus, use of the nitrile intermediate is much preferred since the cis-nitrile is thermally stable and the nitrile group is a good activating group in the Diels-Alder reaction by which this class of intermediates is prepared. When R is a bicyclooctene nucleus, use of the aldehyde intermediate is preferred.

The compounds of formula (IX) are readily converted to compounds of formula (I), or primary amino analogues thereof, by reduction, although, when R$^3$ and R$^4$ represent a single bond, precautions must be taken to avoid reduction of the olefinic moiety. In the case of the nitriles and amides of formula (IX), the reduction is preferably carried out using a complex hydride reducing agent such as lithium aluminium hydride or sodium borohydride, whilst in the case of the isocyanates of formula (IX), treatment with a concentrated mineral acid such as hydrochloric acid produces the desired conversion. The aldehydes and esters of formula (IX) may be reductively aminated to the desired compounds of formula (I) by reduction to the corresponding alcohols, for example, using a complex hydride reducing agent, conversion of the alcohols to the corresponding alkyl or aryl sulphonates (by reaction with an alkyl or aryl sulphonyl chloride such as methyl sulphonyl chloride or p-toluene sulphonyl chloride) and reaction of the sulphonates with an amine of formula HNR$^1$R$^2$. Reductive amination of the aldehydes of formula (IX) may also be carried out by catalytic hydrogenation in the presence of ammonia or an amine of formula HNR$^1$R$^2$.

Alternatively, compounds of formula (IX) where Z' is —CHO may be condensed directly with an amine to give the corresponding Schiffs base which can be reduced with a complex hydride, preferably sodium borohydride, to give a compound of formula (I) in which R$^2$ is hydrogen.

Where Z' is —CN, —CONH$_2$ or —CH$_2$NCO, or the above-mentioned reductive amination is carried out in the presence of ammonia, the resultant product is a primary amine of formula R—(CH$_2$)$_n$NH$_2$ which can then be alkylated to produce a compound of formula (I)

in which $R^1$ and/or $R^2$ is $C_{1-3}$ alkyl. The alkylation may be carried out in conventional manner, for example by reductive alkylation, reaction with an alkyl halide or sulphate, reaction with an alkyl chloroformate followed by reduction of the resultant urethane or, when methylation is to be carried out, by reaction with formic acid/formaldehyde. Similarly, monoalkylated products of formula (I), i.e. compounds of formula (I) where $R^2$ is hydrogen, can be alkylated to form dialkylated products of formula (I) where $R^2$ is $C_{1-3}$ alkyl.

In the case where $Z'$ is —CN, the compound of formula (I) in which $R^1$ is hydrogen and $R^2$ is $C_{1-3}$ alkyl can be obtained by treatment with the corresponding oxonium salt followed by addition of the corresponding alcohol and reduction with sodium borohydride (see *J. Org. Chem.* 34, 627 (1969).

This reaction may be schematically illustrated:

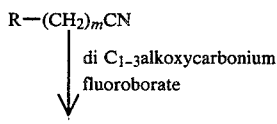

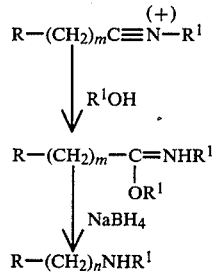

The above intermediates of formula (IX), with the exception of the compound in which R is a bicyclooctane nucleus, m is 0, $Z'$ is —CN and Ar is p-chlorophenyl, are novel and accordingly also form a part of this invention. They may be obtained from the nitrile of formula (X) according to the following reaction sequences in which R, $R^1$, $R^2$, and $R^9$ are as defined above.

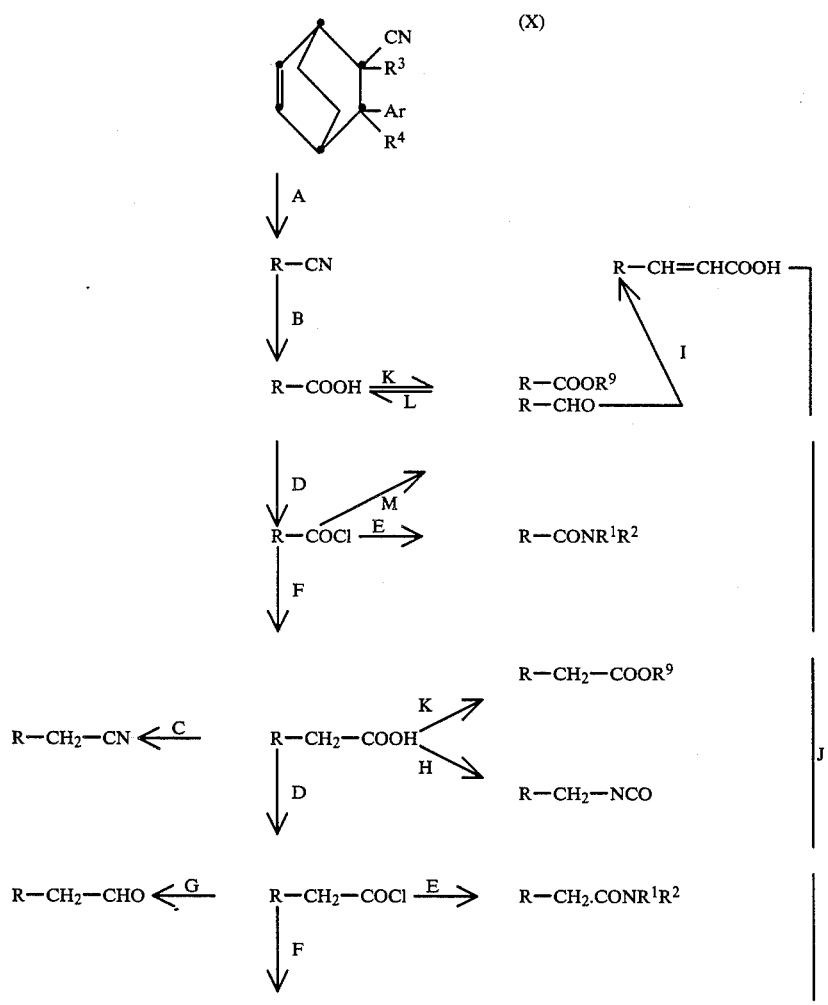

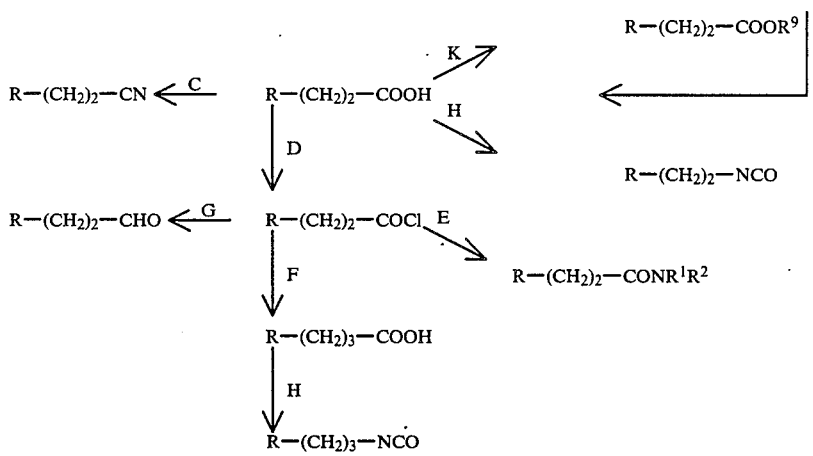

When $R^3$ and $R^4$ are cis-hydrogen atoms, the cis-6-phenyl-bicyclo[2,2,2]oct-2-ene-5-carbonitrile of formula (X) can be prepared by a Diels-Alder reaction between the appropriate cis-cinnamonitrile and 1,3-cyclohexadiene. The cis-cinnamonitrile may be prepared by the route described in *J. Pharm. Sci.*, 54, 1110 (1965) or by decarboxylation of the corresponding benzalycyanoacetric acid.

When $R^3$ and $R^4$ represent a single bond, the nitrile of formula (X) may be prepared from the corresponding aldehyde of formula (XI):

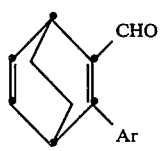 (XI)

by reaction of hydroxylamine followed by dehydration of the oxime thus formed with any suitable dehydrating agent, for example, $P_2O_5$ or cyanuric chloride.

Alternatively, and preferably, the aldehyde of formula (XI) is directly converted to the acid of formula RCOOH by selective hydrogenation followed by treatment of the partially reduced aldehyde with Jones Reagent ($Na_2Cr_2O_7/H_2SO_4$).

The aldehyde of formula (XI) may be prepared by a Diels-Alder reaction between the appropriate phenyl propargyl aldehyde and 1,3-cyclohexadiene.

Reaction A above involves the reduction of the compound of formula (X) using, or example, hydrogen in the presence of a suitable catalyst such as palladium on charcoal, to produce the nitrile of formula (IX) in which m is 0. Clearly, when $R^3$ and $R^4$ represent a single bond, selective hydrogenation must be employed, the reaction being stopped after uptake of one mole of hydrogen. Reaction B is accomplished by hydrolysis as is well known in the art and the resultant carboxylic acid may then be converted to the corresponding acid chloride—reaction D—in conventional manner, for example, by reaction with thionyl chloride. The latter may then be converted by the ArndtEistert synthesis—reaction F—to a substituted acetic acid and, by repetition of reactions D and F, the correspondingly substituted propionic and butyric acid may be obtained. The aforementioned substituted propionic acid may also be prepared from the aldehyde R-CHO by reactions I and J, reaction I being the well-known Knoevenagel reaction to produce a 3-substituted acrylic acid and reaction J involving the reduction of the acrylic acid using, for example, hydrogen over a palladium catalyst to produce the desired propionic acid.

By reaction C, the aforementioned carboxylic acid, substituted acetic acid or substituted propionic acid may be converted to the corresponding nitriles of formula (IX) in which m is 0, 1 or 2. Reaction C may be carried out by treatment of the acid with ammonia at elevated temperatures in the presence of alumina.

The acid chlorides produced by reaction D above are readily converted—reaction E—to the desired amides of formula (IX) by reaction with the appropriate amine of formula $HNR^1R^2$. Additionally by reduction of substituted acetyl and propionyl chlorides produced above—reaction G—the required aldehydes of formula (IX) in which m is 1 or 2 may be obtained. The well known Rosenmund reaction provides one means of accomplishing this reduction.

The above-mentioned substituted acetic, propionic and butyric acids may also be converted—reaction H—to the deired isocyanates of formula (IX) in which m is 0, 1 or 2. This conversion may be accomplished by forming the corresponding acid azide either by treatment of the corresponding acid chloride with sodium azide or by formation of the corresponding acid hydrazide and treatment of the latter with nitrous acid, and then heating the acid azide in benzene or chloroform solution.

Reaction K involves the conventional esterification of the corresponding acid, for example, by reaction with an alcohol $R^9$—OH. The esters of the formula (IX) in which m is 0 can also be prepared by the following reaction sequence:

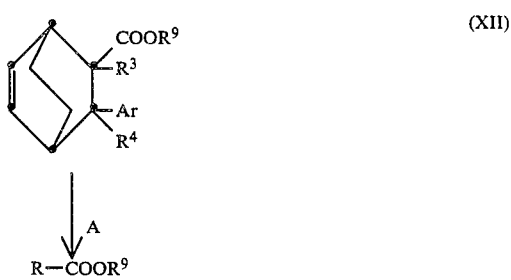 (XII)

wherein reaction A is as described above, the compound of formula (IX) where R is a bicyclooctane nucleus being obtained by a Diels-Alder reaction between the appropriate cis-cinnamonitrile and 1,3-cyclohexadiene, followed by hydrolysis and subsequent esterification. The resultant ester may then be hydrolysed—reaction L—to yield the corresponding acid.

Reaction M can be accomplished by the well-known Rosenmund reduction.

The compounds of formula (I) may also be prepared by the reduction of an olefin of formula (VI) as hereinbefore defined.

This reduction may be effected using hydrogen over a catalyst such as a group VIII metal, for example, platinum or palladium. The catalyst may be supported on an inert carrier, for example, charcoal. To cary out the reaction the unsaturated compound of formula (VI) may be dissolved in a suitable inert solvent, for example, ethanol or ethyl acetate. When it is desired to form a compound of formula (I) in which $R_3$ and $R^4$ represent a single bond, selective hydrogenation of the $R^7/R^8$ olefinic group must be accomplished.

Compounds of formula (VI) are novel. They may be prepared from compounds of formula (XIII);

(XIII)

where $R^7$ and $R^8$ are as defined for formula (VI) and wherein Z' is —CHO, —CO$_2$H, —CO$_2R^9$ or —CN by any of the methods described above for converting the same Z' groups, in the compound of formula (IX) to —NR$^1$R$^2$, provided, of course, that such manipulations do not destroy the unsaturated nature of the bicyclooctene moiety.

Compounds of formula (XIII) in which $R^3$ and $R^4$ taken together represent a single bond, $R^7$ and $R^8$ represent hydrogen atoms and Z' represents an aldehyde group may be prepared:
1. By a Diels-Alder reaction between the appropriate trans-cinnamaldehyde and 1,3-cyclohexadiene followed by catalytic reduction, brominaton with cupric bromide, and subsequent dehydrobromination, preferably with a lithium chloride - lithium carbonate mixture; or
2. By a Diels-Alder reaction between the appropriate phenyl propargyl aldehyde and 1,3-cyclohexadiene followed by catalytic reduction.

Compounds of formula (XIII) where $R^7$ and $R^8$ taken together represent a single bond and Z' is —CHO may be prepared by a Diels-Alder reaction between 1,3-cyclohexadiene and an aldehyde of formula ArR$^4$C=CR$^3$CHO.

The acid, acid chloride, ester and nitrile analogues may be similarly prepared using appropriate modifications of the above synthetic procedures. Preparation of the compounds of formula (XIII) in which $R^7$ and $R^8$ represent a single bond, $R^3$ and $R^4$ represent cis-hydrogen atoms and Z' is nitrile, has already been described hereinabove. Such compounds can be converted into the corresponding acid, ester derivatives, etc., by the methods indicated previously for the compound of formula (X) except, of course, that the reduction step A should be omitted.

A further method of preparing the amines of formula (I) involves the condensation of a compound of formula (VIII):

$$R-(CH_2)_n-Q \qquad \text{(VIII)}$$

where Q is a leaving group being a reactive atom such as a halogen atom, e.g. an iodine atom, or a reactive group such as a sulphonate, e.g. mesyl or tosyl, group, with an amine of formula:

$$HNR^1R^2$$

where R, $R^1$ and $R^2$ are as defined above.

The above type of reaction is well-known in the art and any skilled art worker will immediately appreciate the nature of the reaction conditions necessary to effect the reaction and the identity of suitable Q radicals. However, in passing, it may be mentioned that since the reaction proceeds with elimination of HQ, presence of a proton acceptor such as a base is advisable. If desired, the reaction may be carried out in the presence of a suitable solvent such as methylenedichloride, or dimethyl sulphoxide.

The compounds of formula (VIII) may be derived from the corresponding alcohols of formula (XIV):

$$R(CH_2)_nOH \qquad \text{(XIV)}$$

For example, to obtain a compound of formula (VIII) in which Q is chlorine the above alcohol may be reacted with phosphorous pentachloride or oxychloride and to obtain such a compound in which Q is tosyl or mesyl, the alcohol may be reacted with p-toluene sulphonyl chloride or methyl sulphonyl chloride.

The alcohols of formula (XIV) may be derived from aldehydes of formula:

$$R(CH_2)_mCHO$$

by reduction using an alkali metal borohydride such as sodium borohydride or lithium aluminium hydride.

The intermediates of formula (VIII) and XIV) are novel compounds and are thus provided in a further aspect of the invention.

The compounds of formula (I) produced by the foregoing processes may be isolated per se or in acid-addition salt form.

The acid-addition salts are preferably the pharmaceutically acceptable, non-toxic addition salts with suitable acids, such as those with inorganic acids, for example, hydrochloric, hydrobromic, nitric, sulphuric or phosphoric acids, or with organic acids, such as organic carboxylic acids, for example, glycolic, maleic, hydroxmaleic, malic, tartaric, citric, salicylic, o-acetoxybenzoic, nicotinic or isonicotinic acid, or organic sulphonic acids such as for example, methanesulphonic, ethanesulphonic, 2-hydroxyethanesulphonic, p-toluenesulphonic, or 2-naphthalenesulphonic acid. Apart from pharmaceutically acceptable acid-addition salts, other salts are also included within the scope of acid-addition salts such as, for example, those with picric or oxalic acid; they may serve as intermediates in the purification of the compounds or in the preparation of other, for example, pharmaceutically acceptable, acid-addition salts, or are useful for identification, characterization or purification of the bases.

A resulting acid-addition salt may be converted into the free compound according to known methods, for example, by treating it with a base, such as with a metal hydroxide or alkoxide, for example, an alkali-metal or alkaline-earth-metal hydroxide, for example, lithium hydroxide, sodium hydroxide, potassium hydroxide or calcium hydroxide; with a metal carbonate, such as an alkali-metal or an alkaline-earth-metal carbonate or hydrogen carbonate, for example, sodium, potassium or calcium carbonate or hydrogen carbonate; with ammonia; or with a hydroxyl ion-exchange preparation; or with any other suitable reagent.

A resulting acid-addition salt may also be converted into another acid-addition salt according to known methods; for example, a salt with an inorganic acid may be treated with a metal salt, for example a sodium, barium or silver salt, of an acid in a suitable diluent, in which a resulting inorganic salt is insoluble and is thus removed from the reaction medium. An acid-addition salt may also be converted into another acid-addition salt by treatment with an anion exchange preparation.

As stated previously, when $R^3$ and $R^4$ represent cis-hydrogen atoms, the compound of formula (I) may exist in two enantiomeric forms. Although the racemate possesses antidepressant activity in its own right, in certain circumstances it may be desirable to resolve the racemate into its dextrorotatory (+) and laevorotatory (−) forms. The resolution may be effected by any method conventionally used in the resolution of optically active bases, such as by reaction with optically active acids of known stereochemistry, followed by fractional crystallisation of the salts formed. Suitable optically active acids which may be mentioned are (+) or (−) tartaric, malic, mandelic or camphorsulphonic acid, use of the latter acid being preferred. It has been found that the (+)-enantiomers of the compounds of formula (I) have particularly specific CNS activity.

The compounds of formula (I), and pharmaceutically-acceptable acid-addition salts thereof, possess antidepressant activity and hence are useful for the treatment of various depressive states in mammals. Their usefulness has been demonstrated in well-known test procedures such as antagonism of reserpine hypothermia in mice and inhibition of re-uptake of noradrenaline (NA) and 5-hydroxytryptamine (5HT) in mouse brain synaptosomes. They have low toxicity.

The compounds of this invention differ from most existing antidepressant drugs in that they not only inhibit norepinephrine uptake but in addition are extremely potent inhibitors of dopamine uptake. There is increasing evidence that depressed patients form a heterogeneous group in terms of neural deficiencies [see J. W. Maas, "Clinical and Biochemical Heterogeneity of Depressive Disorders," *Ann Int. Med.* 88, 556–563 (1978)]and that antidepressant drugs with different spectra of activity as amine uptake inhibitors affect different subroups of depressed patients preferentially [see P. J. Lewi and F. C. Colpaert, "On the Classification of Antidepressant Drugs," *Psychopharmacology* 49, 219–224 (1976)].

As noted above, the active compounds of the present invention form acid-addition salts and, where such salts are pharmaceutically-acceptable, they are equally useful for the treatments mentioned herein. The active compounds and the pharmaceutically-acceptable acid-addition salts thereof of this invention are effective over a wide dosage range, the actual dose administered being dependent on such factors as the particular compound being used, the condition being treated and the type and size of mammal being treated. However, the dosage per day required will normally fall within the range of 0.1 to 20 mg/Kg. In the treatment of adult humans, single dosages of from 0.1 to 5 mg/Kg. may be used whilst, in the treatment of test animals such as mice and rats, single dosages of from 1 to 50 mg/Kg. may be employed.

The active compounds and salts of the present invention will normally be administered orally or by injection and, for this purpose, said compounds and salts will usually be utilized in the form of a pharmaceutical composition. Such compositions are prepared in a manner well known in the pharmaceutical art and normally comprise at least one active compound or salt of the invention in association with a pharmaceutically-acceptable carrier therefor. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxybenzoate, talc, magnesium stearate or mineral oil. The compositions of the invention may, as is well known in the art, be formulated so as to provide quick, sustained or delayed release of the active ingredient after administration to the patient.

Depending on the route of administration, the foregoing compositions may be formulated as tablets, capsules or suspensions for oral use and injection solutions for parenteral use. Preferably the compositions are formulated in a dosage unit form, each dosage containing from 1 to 500 mg., more usually 5 to 250 mg., of the active ingredient.

Accordingly, in one aspect of the invention there is provided a pharmaceutical composition which comprises a compound of formula (I) or a pharmaceutically-acceptable acid-addition salt thereof, associated with a pharmaceutically-acceptable carrier therefor.

In a further aspect of the invention there is provided a method of preparing a pharmaceutical composition as described above which comprises admixing a compound of formula (I), or a pharmaceutically-acceptable acid-addition salt thereof, with a pharmaceutically-acceptable carrier therefor.

In yet a further aspect of the invention there is provided a method of treating depressive states in mammals, particularly humans, which comprises administering a chemotherapeutically effective amount of a compound of formula (I), or a pharmaceutically-acceptable salt thereof, to the afflicted mammal.

It is to be clearly understood that the preferred features set out below the initial discussion of the compounds of formula (I) hereinbefore, apply mutatis mutandis to all other aspect of the invention.

The invention will now be illustrated with references to the following examples.

EXAMPLE 1 cis-3-N,N-Dimethylaminomethyl-2-(o-chlorophenyl)-bicyclo-[2,2,2]octane hydrochloride (a) cis-o-Chlorocinnamonitrile o-Chlorobenzalcyanoacetic acid (40 g; 0.193 m) was intimately mixed with copper powder (3 g) and cuprous oxide (1 g) and heated in vacuo at a temperature of 240° C. with vigorous evolution of carbon dioxide. The distillate was a pale yellow oil which was shown to contain 71% cis-nitrile by NMR assay. Fractional distillation of the mixture was carried out collecting early fractions containing pure cis-isomer, b.p. 90°–92° C. at 1.2 mm/Hg.

(b) cis-5-(o-Chlorophenyl)-6-cyanobicyclo[2,2,2]oct-2-ene cis-o-Chlorocinnamonitrile (13 g; 80 mmole) and 1,3-cyclohexadiene (11.43 ml; 120 mmole) were added to a sealed tube with a trace of hydroquinone and 1,2-dichlorobenzene, and heated at 150°–160° C. for 2 weeks. The product oil was washed several times with cold 40°–60° C. petrol, after having highly boiling solvents initially removed, and then repeatedly washed with hot 60°–80° C. petrol. These latter washings were collected and reduced to a viscous oil (15 g. crude; 77%). Crystallization of a small part of this oil gave a white crystalline solid (m.p. 105°–106° C). The remainder was used in the next section.

(c) cis-2-(o-Chlorophenyl)-3-cyanobicyclo[2,2,2]octane

Crude cis-5-(o-chlorophenyl)-6-cyanobicyclo[2,2,2]oct-2-ene (5.9 g; 243 mmole) was dissolved in absolute ethanol (40 ml) and reduced at atmospheric pressure over 5% Palladium/charcoal (0.6 g; 10% by weight). After the theoretical amount of hydrogen uptake, the catalyst was filtered off and the solution reduced to an oil (4.72 g; 80%). Recrystallization from ethanol yielded a white crystalline solid (m.p. 96°–98° C.).

(d) cis-3-Aminomethyl-2-(o-chlorophenyl)bicyclo[2,2,2]octane hydrochloride cis-2-(o-Chlorophenyl)-3-cyanobicyclo[2,2,2]octane (4.0 g; 16.4 mm) in dry tetrahydrofuran (10 ml) was added dropwise to a chilled and stirred solution of lithium aluminium hydride (0.87 g; 23.2 mm) in dry tetrahydrofuran (20 ml). After the addition, the solution was allowed to warm to room temperature and was stirred overnight. After the addition of water, the solution was decanted from solid material which was washed with ether. The solutions were combined then washed with 2N HCl. The aqueous layer was separated, basified with 2N NaCH solution, and the amine extracted using ethyl acetate. After drying the combined extracts over magnesium sulphate, filtration and removel of solvent produced an oil which on dissolving in ethanolic hydrochloric acid and slowly adding ether gave the title compound (2.8 g) m.p. 220°–223° C.

(e) cis-3-N,N-Dimethylaminomethyl-2-(o-chlorophenyl)bicyclo[2,2,2]octane hydrochloride To cis-3-aminomethyl-2-(o-chlorophenyl)bicyclo[2,2,2]octane (2.3 g; 8.1 mm) was added sodium hydrogen carbonate (1.55 g; 18.5 mmole) and dimethylformamide (50 ml). The flask was cooled in ice and a mixture of formic acid 90% (2.03 ml; 45 m) and formaldehyde (3.87 ml; 45 mmole) added slowly. After the addition, the solution was slowly heated to reflux. After 4 hours, the solution was cooled, added to water (50 ml), made alkaline (pH=8) with solid potassium hydroxide and extracted with ethyl acetate. The combined ethyl acetate layer was washed with water, dried over magnesium sulphate, filtered and subjected to reduced pressure so as to yield a brown oil (2.2 g). The salt was formed from ethanolic hydrochloric acid and recrystallized from ethanol/ether mixture (1.7 g; m.p. 215°–217° C.).

EXAMPLE 2 cis-3-N,N-Dimethylaminomethyl-2-phenylbicyclo[2,2,2]octane, hydrochloride, m.p. 220°–223° C., was similarly prepared.

EXAMPLE 3 cis-3-N,N-Dimethylaminomethyl-2-(p-fluorophenyl)-bicyclo[2,2,2]octane, hydrochloride cis-3-Aminomethyl-2-(p-fluorophenyl)bicyclo[2,2,2]octane (3 g; 0.0128 m) [prepared as in Example 1(d), except that the p-fluorocinnamonitrile was prepared from p-fluorobenzaldehyde and cyanoacetic acid by the procedure outlined in *Organic Reactions,* 15 374–381], acetic acid (30 ml), ethanol (30 ml), 40% formaldehyde in water (10 ml, 0.051 m) and 5% Palladium on charcoal (1 g) were hydrogenated in a Parr apparatus (60 lbs/inch$^2$). After four hours, the catalyst was filtered off and the filtrate evaporated. The oil was dissolved in dilute hydrochloric acid and extracted with ether. The acid extracts were basified (5N NaOH) and extracted with ether. The ether was washed, ($H_2O$), dried ($MgSO_4$) and evaporated to give an oil (2.6 g, 80.4%) which, on dissolving in ethanolic hydrogen chloride and adding ether, produced the hydrochloride salt. Yield 1.9 g, (50%); m.p. 232°–234° C.

EXAMPLE 4 cis-2-(p-Fluorophenyl)-3-N-methylaminomethyl-bicyclo[2,2,2]octane, hydrochloride To a mixture of cis-3-aminomethyl-2-(p-fluorophenyl)bicyclo[2,2,2]octane (1.34 g; 0.006 m) prepared in a similar manner to Example 1(d), and sodium carbonate (7.92 g; 0.078 m) in ether (25 ml) at 0° C., was added trifluoroacetic anhydride (12.0 g; 0.06 m) dropwise. After stirring at room temperature for two hours, the mixture was poured into ice/water and extracted with chloroform. The chloroform was washed (water, dried ($MgSO_4$) and evaporated to give an oil (2 g). After dissolving the oil in acetone (50 ml), methyl iodide (4.6 g; 0.03 m) then potassium hydroxide (1.4 g; 0.03 m) were added followed by reflux for one hour. After evaporation, the residue was added to water (50 ml) and refluxed for twenty minutes. After extracting with ether, the ether was washed, dried, and evaporated to give an oil which, on dissolving in ethanolic hydrogen chloride and adding ether, produced white crystals. Yield 0.4 g (24.6%) m.p. 236°–238° C.

EXAMPLE 5

(a) cis-3,4-Dichlorocinnamonitrile 3,4-Dichlorobenzaldehyde (175 gms; 1 m), cyanoacetic acid (100 g; 1.15 m), and pyridine were refluxed for one day. Evaporation produced an oil which was fractionally distilled using a column (1 ft. long, ½ inch diameter) filled with glass helices. Overall yield 88.9 g (45%; 30% cis/70% trans).

Yield of isolated pure cis isomer: 17 g (9%) m.p. 60°–60.5° C.: b.p. 110° C. at 0.15 mm.

Only pure cis-isomer was used in the next stage (b).

(b) cis-6-Cyano-5-(3,4-dichlorophenyl)bicyclo[2,2,2]oct-2-ene 1,3-Cyclohexadiene (60% solution, 13.8 g, 0.17 m), cis-3,4-dichlorocinnamonitrile (17 g, 0.085 m) and benzene (10 ml) were heated in a sealed tube in the presence of a few crystals of hydroquinone at 160° C. After 17 days, the solution was evaporated and the residue was extracted with hot petrol (60°–80° C). The petrol was evaporated to give a solid which was recrystallized from ethanol to give large crystals of the title compound. Yield 12.3 g (51.5%) m.p. 115°–116° C.

(c) cis-3-Cyano-2-(3,4-dichlorophenyl)bicyclo[2,2,-2]octane cis-6-Cyano-5-(3,4-dichlorophenyl)bicyclo[2,2,2]oct-2-ene (12 g; 0.043 m) in ethanol (50 ml) and chloroform (30 ml) was hydrogenated at 60 lb/inch$^2$ in the presence of 5% Palladium on charcoal (1.2 g). The catalyst was filtered off and the filtrate evaporated to give the title compound as a solid (12 g) which was recrystallized from ethanol. Yield 8.4 g (70%), m.p. 82°–83° C.

(d) cis-3-Aminomethyl-2-(3,4-dichlorophenyl)bicyclo[2,2,2]octane, hydrochloride

To lithium aluminum hydride (0.8 g; 0.021 m) in ether (50 ml), cis-3-cyano-2-(3,4-dichlorophenyl)bicyclo[2,2,-2]octane (4 g; 0.014 m) in tetrahydrofuran (30 ml) was added dropwise at 0° C. After four hours, 5N NaOH (1 ml) then water (4 ml) was added cautiously to produce a fine white precipitate which was filtered. The filtrate was dried and evaporated to produce an oil. On adding ethanolic hydrogen chloride, white cyrstals of the hydrochloride salt were produced. Yield 3 g (65.6%) m.p. 274°–277° C.

(e) cis-2-(3,4-Dichlorophenyl)-3-N-methylaminomethylbicyclo[2,2,2]octane hydrochloride cis-3-Cyano-2-(3,4-dichlorophenyl)bicyclo[2,2,2]octane (0.9 g; 0.0032 m), dimethoxycarbonium fluoroborate (0.8 g; 0.0128 m) and dichlormethane (24 ml) were refluxed with stirring for one day. The mixture was cooled to 0° C. and ethanol (4 ml) added followed by evaporation. The residue was dissolved in methanol (15 ml) and, at 0° C. sodium borohydride (0.75 g, 0.02 m) added carefully. After 1 hour at 0° C. the mixture was acidified with 5N HCl and evaporated. The residue was diluted with water and extracted with ether. The aqueous part was basified (5N NaOH) and extracted with ether. The ether was washed, dried and evaporated to give an oil which on dissolving in ethanolic hydrogen chloride gave the title product as white needles. Yield 0.72 g (67%) m.p. 247°–248° C.

EXAMPLE 6 cis-3-N-Methylaminomethyl-2-phenylbicyclo[2,2,2]octane, hydrochloride cis-3-Cyano-2-phenylbicyclo[2,2,2]octane (2.1 g; 0.01 m) prepared as in Example 1(c), dimethoxycarbonium fluoroborate (3.2 g; 0.02 m) and dichloromethane (25 ml) were refluxed with stirring for one day. The mixture was cooled to 0° C. and ethanol (3 ml) added followed by evaporation. The residue was dissolved in methanol (25 ml) and, at 0° C., sodium borohydride (2 g; 0.05 m) added carefully. After 1 hour at 0° C. the mixture was acidified with 5N HCl and evaporated. The residue was diluted with water and extracted with ether. The aqueous part was basified with 5N NaOH and extracted with ether. The ether was washed, dried (MgSO$_4$) and evaporated to give an oil which on dissolving in ethanolic hydrogen chloride gave white needles. Yield 1 g (38%) m.p. 213°–215° C.

EXAMPLE 7

3-N,N-Dimethylaminomethyl-2-phenylbicyclo[2,2,-2]oct-2-ene, hydrochloride (a) 3-Formyl-2-phenylbicyclo[2,2,2]oct-2,5-diene 1,3-Cyclohexadiene (70% solution, 10 ml, 0.09 m) and phenylpropargyl aldehyde (4 g; 0.03 m) were refluxed in the presence of a few crystals of hydroquinone for 5 days. The solution was evaporated and the residue distilled. Yield 3.8 g (61%) b.p. 110°–120° C. at 0.1 mm. NMR showed the mixture to contain 75% of the required product.

(b) 3-Formyl-2-phenylbicyclo[2,2,2]oct-2-ene

3-Formyl-2-phenylbicyclo[2,2,2]octa-2,5-diene (3.7 g; 0.018 m) 5% Palladium on charcoal (0.3 g) and ethyl acetate (100 ml) were hydrogenated for 1 week. The catalyst was filtered off and the filtrate evaporated, then the residue distilled twice; Yield 1.9 g (51%) b.p. 160° C. at 0.2 mm/Hg.

(c) 3-Formyl-2-phenylbicyclo[2,2,2]oct-2-ene (alternative method)

trans-3-Formyl-2-phenylbicyclo[2,2,2]octane (107 g; 0.05 m) in chloroform (50 ml) was added to cupric bromide (22.3 g; 0.1 m) in ethyl acetate (50 ml). The mixture was refluxed for four hours, left overnight at room temperature, treated with charcoal and evaporated to give 3-bromo-3-formyl-2-phenylbicyclo[2,2,-2]octane as a brown oil (m.p. 65°–66° C. after crystallization from ethanol). The oil was dissolved in dimethylformamide (50 ml) and lithium bromide (5 g; 0.057 m) and lithium carbonate (5 g; 0.078 m) were added, refluxing the mixture for 2 hours. After pouring in water (600 ml) and extracting with ether, the ether was washed, dried (MgSO$_4$) and evaporated to give an oil which was distilled. Yield 8.3 g, (76%) b.p. 160° C. at 0.2 mm/Hg.

(d) 3-Hydroxymethyl-2-phenylbicyclo[2,2,2]oct-2-ene

To lithium aluminium hydride (1 g; 0.03 m) in ether (50 ml) was added 3-formyl-2-phenylbicyclo[2,2,2]octane (4.2 g; 0.02 m) in ether (40 ml) dropwise at 0° C. After 1 hour, 5N sodium hydroxide (1 ml) followed by water (5 ml) was added cautiously. After filtering, the filtrate was evaporated to give an oil which was used directly in (e) below.

(e) 3-N,N-Dimethylaminomethyl-2-phenylbicyclo[2,2,2]oct-2-ene, hydrochloride

To 3-Hydroxymethyl-2-phenylbicyclo[2,2,2]oct-2-ene (1.4 g; 0.008 m) in dichloromethane (20 ml) and triethylamine (5 ml) at 0° C. methanesulphonyl chloride (2.4 ml, 20% excess) was added dropwise. After one day at 0° C., the mixture was poured into ice and extracted with dichloromethane. The dichloromethane was dried (MgSO$_4$) and evaporated to give an oil (1.7 g). The oil was dissolved in dichloromethane (20 ml) and added to dimethlamine (15 ml of 30% solution in ethanol) at 0° C. After stirring at room temperature for 3 days, the solution was evaporated and the residue dissolved in 5N HCl and extracted with ether. The ether was dried (MgSO$_4$) and evaporated to give an oil (0.5 g) which on dissolving in ethanolic hydrogen chloride produced white needles. Yield 0.48 g (26%) m.p. 236°–237° C.

EXAMPLE 8 cis-2-(3,4-Dichlorophenyl)-3-N,N-dimethylaminomethylbicyclo[2,2,2]octane, hydrochloride cis-3-Aminomethyl-2-(3,4-dichlorophenyl)bicyclo[2,2,2]octane hydrochloride (4 g; 0.012 m) acetic acid (30 ml), ethanol (30 ml), 40% formaldehyde in water (20 ml, 0.1 m) and 5% Palladium on charcoal (1 g) were hydrogenated in a Parr apparatus (60 lbs/inch$^2$). After five hours the catalyst was filtered off and the filtrate evaporated. The oil was dissolved in dilute hydrochloric acid and extracted with ether. The aqueous extracts were basified (5N NaOH) and extracted with ether. The ether was washed (H$_2$O), dried (MgSO$_4$) and evaporated to give an oil which, on dissolving in ethanolic hydrogen chloride and adding ether, produced the title compound. Yield 3.2 g (74%), m.p. 223°–225° C.

EXAMPLE 9

(+) and (−) cis-2-(3,4-Dichlorophenyl)-3-N,N-dimethylaminomethylbicyclo[2,2,2]octane, hydrochloride The amine hydrochloride product of Example 8 was dissolved in hot water containing sufficient ethanol for solubilisation. Excess potassium carbonate solution was then added and the mixture agitated. The free base thus liberated was then extracted with ether, the ether extracts dried with magnesium sulphate, filtered and evaporated to yield an oil which crystallized on standing for a few days.

The crystalline free base was then dissolved in cold ethyl acetate (2.63 g; in 25 ml) containing ethanol (2.5 ml). D-(+)-Camphorsulphonic acid (1.95 g) dissolved in hot ethyl acetate (25 ml) was added to this solution. The combined solution was stirred slowly until white crystals of the acid/amine salt came out of solution. The reaction mixture was then allowed to stand for 24 hours and the salt recovered by filtration. This salt was repeatedly recrystallized from ethyl acetate and ethanol until a constant melting point and specific rotation were obtained. $[\alpha]_D^{23} = +81°$ (C=0.5%, EtOH); m.p. 219° C.

The pure camphorsulphonic acid/amine salt was then dissolved in hot water and excess potassium carbonate added to liberate the free base, which was extracted with ether. The combined ether extracts were dried, filtered and evaporated to an oil. This oil was dissolved in ethanol. HCl was then added to the solution followed by sufficient ether to allow crystallization of the hydrochloride salt overnight. The white HCl salt which formed was (+)-cis-2-(3,4-dichlorophenyl)-3-N,N-dimethylaminomethylbicyclo[2,2,2]octane, hydrochloride.

$[\alpha]_D^{22} = +99°$ (C=0.4%, EtOH); m.p. 224°–226° C.

Similarly, using a modification of the above resolution method there was obtained:

(−)-cis-2-(3,4-dichlorophenyl)-3-N,N-dimethylaminomethylbicyclo[2,2,2]octane, hydrochloride.
$[\alpha]_D^{22} = -99°$ (C=0.4%, EtOH)

EXAMPLE 10

3-N-methylaminomethyl-2-(3,4-dichlorophenyl)bicyclo[2,2,2]oct-2-ene, hydrochloride (a) trans-3-Formyl-2-(3,4-dichlorophenyl)bicyclo[2,2,2]oct-5-ene trans-3,4-Dichlorocinnamaldehyde [*J. Med. Chem.* 14, 797 (1971)] (71.9 g; 0.36 m), 1,3-cyclohexadiene (56 ml of a 70% solution, 0.45 m) and benzene (25 ml) were heated in a sealed tube in the presence of a few crystals of hydroquinone at 180° C. After 4 days, the solution was evaporated and the residue purified by bulb to bulb distillation to give the title compound as a yellow oil, yield 62 g; b.p. 200° C. at 0.1 mm/Hg.

(b) trans-3-Formyl-2-(3,4-dichlorophenyl)bicyclo[2,2,2]octane trans-3-Formyl-2-(3,4-dichlorophenyl)bicyclo[2,2,-2]oct-5-ene (62 g; 0.218 m) was hydrogenated in ethyl acetate (400 ml) at atmospheric pressure in the presence of 5% Pd/C (6.2 g). After 3 hours the catalyst was filtered off and the filtrate evaporated to give the title compound as an oil which was crystallized from petroleum ether (60°–80° C.), yield 51.3 g (81%); m.p. 73°–74° C.

(c) 3-Formyl-2-(3,4-dichlorophenyl)bicyclo[2,2,-2]oct-2-ene

Cupric bromide (45.7 g; 0.205 m) was added to trans-3-formyl-2-(3,4-dichlorophenyl)bicyclo[2,2,2]octane (29 g; 0.102 m) dissolved in a mixture of chloroform (355 ml) and ethyl acetate (355 ml). After refluxing for 2 hours the solution was filtered and the filtrate evaporated to give 3-bromo-2-(3,4-dichlorophenyl)-3-formyl-bicyclo[2,2,2]octane as a brown oil. This oil was dissolved in dimethylformamide (350 ml) and lithium bromide (17.8 g; 0.204 m) and lithium carbonate (15.2 g; 0.204 m) added, refluxing the mixture for 2 hours. After pouring the solution into water (3 liters) and extracting with dichloromethane, the dichloromethane extract was washed, dried (MgSO$_4$) and evaporated to give an oil (31 g) which was purified by bulb to bulb distillation. Yield 25.3 g (88%); b.p. 190° C. 0.1 mm/Hg.; m.p. 71°–71.5° C. (after crystallization from petroleum ether, 60°–80° C.).

(d) N-{2-(3,4-Dichlorophenyl)bicyclo[2,2,2]oct-2-ene-3-yl}-methylidene-methylamine A 33% solution of methylamine in ethanol (250 ml) was added in one lot to 3-formyl-2-(3,4-dichlorophenyl)bicyclo[2,2,2]oct-2-ene (25 g; 0.089 m) in dichloromethane (50 ml) at 0° C. After 1 hour, the solution was evaporated to yield an oil. Yield 26 g. (100%). An infrared spectrum showed complete loss of the carbonyl group. A peak at 1630 cm$^{-1}$ indicated the presence of an imine (—CH=N—Me group). M+ 293/295.

(e) 3-N-Methylaminomethyl-2-(3,4-dichlorophenyl)-bicyclo[2,2,2]oct-2-ene, hydrochloride Sodium borohydride (6 g., 0.162 m) was added to N-{2-(3,4-dichlorophenyl)bicyclo[2,2,2]oct-2-ene-3-yl}-methylidene-methylamine (26 g; 0.089 m) in methanol (250 ml) at 0° C. over a period of forty-five minutes, the mixture being stirred at room temperature overnight. The methanol was evaporated off, the residue dissolved in dilute hydrochloric acid and the mixture extracted with ether. The aqueous parts was basified (5N NaOH) and extracted with ether. The ether was washed (H$_2$O), dried (MgSO$_4$) and evaporated to give a colourless oil (21.4 g, 81.3%). A sample of the product was dissolved in ethanolic hydrogen chloride and ether was added to give the title compound, m.p. 247.0°–249° C.

(f) 3-N,N-Dimethylaminomethyl-2-(3,4-dichlorophenl)bicyclo[2,2,2]oct-2-ene hydrochloride A mixture of 90% formic acid (18.5 ml, 0.36 m) and 37% formaldehyde (29.3 ml, 0.036 m) was added at 0° C. to 3-N-methylaminomethyl-2-(3,4-dichlorophenyl)- bicyclo[2,2,2]oct-2-ene (0.072 m, 21.4 g) in dimethylformamide (36 ml). After refluxing for 5 hours, evaporation produced a colourless residue to which water (1 liter) then 5N HCl was added. After extraction with ether, the aqueous part was basified (5N NaOH) and again extracted with ether. The ether was washed, dried (MgSO$_4$) and evaporated to give a colourless oil which, on dissolving in ethanolic hydrogen chloride followed by addition of ether gave the title product which was crystallized from an IPA/hexane mixture, yield 15.8 g (63%) m.p. 204°–207° C.

EXAMPLES 11 to 14

The following further compounds of the invention were prepared using procedures similar to those described above.

cis-3-N,N-Dimethylaminomethyl-2-(p-bromophenyl)bicyclo[2,2,2]octane, hydrochloride, (m.p. 238° C.)

cis-3-N-Methylaminomethyl-2-(p-bromophenyl)bicyclo[2,2,2]octane, hydrochloride, (m.p. 241° C.).

3-N-Methylaminomethyl-2-(4-chlorophenyl)bicyclo[2,2,2]oct-2-ene, hydrochloride. (m.p. 251°–253° C.)

3-N,N-Dimethylaminomethyl-2-(4-chlorophenyl)bicyclo[2,2,2]oct-2-ene, hydrochloride. (m.p. 195° C.)

The following Examples illustrate pharmaceutical formulations containing compounds of formula (I). The active ingredient used was cis-3-N,N-dimethylaminomethyl-2-(3,4-dichlorophenyl)bicyclo[2,2,2]octane, hydrochloride; however, this compound may be replaced by other active solid compounds of the invention.

EXAMPLE 15

Tablets each containing 5 mg of active ingredient were made up as follows:

| | | |
|---|---|---|
| Active ingredient | 5 mg | |
| Potato starch | 20 mg | |
| Lactose | 20 mg | |
| Polyvinylpyrrolidone (as 10% solution in water) | 2 mg | |
| Sodium starch glycolate | 2 mg | |
| Magnesium stearate | 0.5 mg | |
| Talc | 0.5 mg | |
| Total | 50 mg | |

The starch lactose and active ingredient were passed through a sieve and thoroughly mixed. The solution of polyvinylpyrrolidone was mixed with the resultant mixture and the combination passed through a No. 12 mesh B.S. sieve. The granules so produced were dried at approximately 55° C. and passed through a No. 16 mesh B.S. sieve. The magnesium stearate, sodium starch glycolate and talc, previously passed through a No. 60 mesh B.S. sieve, were then added to the granules which, after mixing, were compressed on a tablet machine to yield tablets each weighing 50 mg.

EXAMPLE 16

Capsules each containing 10 mg of medicament were made as follows:

| | |
|---|---|
| Active ingredient | 10 mg |
| Starch | 44 mg |
| Lactose | 45 mg |
| Magesium stearate | 1 mg |
| Total | 200 mg |

The lactose, starch, magnesium stearate and active ingredient were passed through a No. 44 mesh B.S. sieve and filled into hard gelatin capsules in 100 mg quantities.

EXAMPLE 17

Suppositories each containing 25 mg of active ingredient were made as follows:

| | |
|---|---|
| Active ingredient | 25 mg |
| Saturated fatty acid glycerides to | 2,000 mg |

The active ingredient was passed through a No. 60 mesh B.S. sieve and suspended in the saturated fatty acid glycerides previously melted using the minimum heat necessary. The mixture was then poured into a suppository mould of nominal 2 g. capacity and allowed to cool.

We claim:

1. An amine of formula (I):

$$R-(CH_2)_n-NR^1R^2 \qquad (I)$$

or a pharmaceutically-acceptable acid-addition salt thereof, wherein n is an integer from 1 to 3; $R^1$ is $C_1$-$C_3$ alkyl; $R^2$ is hydrogen or $C_1$-3 alkyl; and R is a 2-phenylbicyclo group of formula:

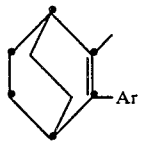

and Ar is selected from the group consisting of phenyl, p-halophenyl or 3,4-dihalophenyl.

2. A pharmaceutical composition comprising as an active ingredient from 1 to 250 mg of a compound of claim 1.

3. A method of treating a mammal suffering from, or susceptible to, a disorder of the central nervous system, which comprises administering to said mammal a chemotherapeutically effective amount of a compound of claim 1.

4. An amine of claim 1 wherein the Ar member is selected from the group consisting of p-chlorophenyl, p-bromophenyl and 3,4-dichlorophenyl.

5. An amine of formula (I) according to claim 1, or a pharmaceutically-acceptable acid-addition salt thereof, wherein $R^1$ and/or $R^2$ is methyl.

6. An amine of formula (I) according to claim 1, or a pharmaceutically-acceptable acid-addition salt thereof, wherein n is 1.

7. The amine of claim 1 which is 3-N,N-dimethylamino-2-(3,4-dichlorophenyl)bicyclo[2,2,2]oct-2-ene, or a pharmaceutically-acceptable acid-addition salt thereof.

8. A pharmaceutical composition according to claim 1 wherein the active ingredient is a compound of formula (I) wherein n is 1, and Ar is selected from the group consisting of p-chloro-, p-bromo- and 3,4-dichlorophenyl.

9. A method according to claim 3, wherein in the amine of formula (I), n is 1 and Ar is p-chlorophenyl, p-bromophenyl or 3,4-dichlorophenyl.

* * * * *

UNITED STATES PATENT AND TRADEMARK OFFICE
CERTIFICATE OF CORRECTION

PATENT NO. : 4705807
DATED : November 10, 1987
INVENTOR(S) : David C. Horwell, et al.

It is certified that error appears in the above-identified patent and that said Letters Patent is hereby corrected as shown below:

Column 20, line 68, should read --

10. The amine of claim 1 which is 3-N-methyl-amino-2-(3,4-dichlorophenyl)bicyclo[2,2,2]oct-2-ene, or a pharmaceutically-acceptable acid-addition salt thereof.--

Signed and Sealed this

Twenty-first Day of March, 1989

Attest:

DONALD J. QUIGG

*Attesting Officer*

*Commissioner of Patents and Trademarks*